(12) United States Patent
Takauchi et al.

(10) Patent No.: US 11,467,069 B2
(45) Date of Patent: Oct. 11, 2022

(54) SAMPLING CHIP DIVIDING INSTRUMENT

(71) Applicant: SHIMADZU CORPORATION, Kyoto (JP)

(72) Inventors: Ippei Takauchi, Kyoto (JP); Shinobu Kudoh, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 616 days.

(21) Appl. No.: 16/475,465

(22) PCT Filed: Jan. 5, 2017

(86) PCT No.: PCT/JP2017/000177
§ 371 (c)(1),
(2) Date: Jul. 2, 2019

(87) PCT Pub. No.: WO2018/127961
PCT Pub. Date: Jul. 12, 2018

(65) Prior Publication Data
US 2021/0131920 A1 May 6, 2021

(51) Int. Cl.
*G01N 1/18* (2006.01)
*G01N 1/28* (2006.01)
*G01N 33/49* (2006.01)

(52) U.S. Cl.
CPC ............... *G01N 1/18* (2013.01); *G01N 1/28* (2013.01); *G01N 33/491* (2013.01)

(58) Field of Classification Search
None
See application file for complete search history.

(56) References Cited

U.S. PATENT DOCUMENTS

| | | | | |
|---|---|---|---|---|
| 4,861,477 | A | 8/1989 | Kimura | |
| 6,855,243 | B2 * | 2/2005 | Khan | G01N 33/525 205/792 |
| 2003/0024811 | A1 * | 2/2003 | Davies | G01N 27/3272 204/403.01 |
| 2003/0211619 | A1 * | 11/2003 | Olson | A61B 5/150419 422/68.1 |
| 2004/0086869 | A1 * | 5/2004 | Schembri | G01N 35/028 506/9 |

(Continued)

FOREIGN PATENT DOCUMENTS

| | | |
|---|---|---|
| JP | 01-199159 A | 8/1989 |
| JP | 02-122800 U | 10/1990 |

(Continued)

OTHER PUBLICATIONS

International Search Report for PCT/JP2017/000177 dated Apr. 4, 2017 [PCT/ISA/210].

(Continued)

*Primary Examiner* — Lore R Jarrett
(74) *Attorney, Agent, or Firm* — Sughrue Mion, PLLC

(57) ABSTRACT

The sampling chip dividing instrument includes: a main body block; a space that is provided inside the main body block, has an opening leading to an outer surface of the main body block, and fits in and contains the cut portion of the sampling chip through the opening; and an surrounding portion that is provided outside the space at a periphery of the opening, and receives a sample scattered from a break portion of the sampling chip divided near the opening.

6 Claims, 6 Drawing Sheets

(56) References Cited

U.S. PATENT DOCUMENTS

| | | | | |
|---|---|---|---|---|
| 2005/0100880 | A1* | 5/2005 | Chang | G01N 33/5438 |
| | | | | 204/403.03 |
| 2008/0118399 | A1* | 5/2008 | Fleming | C12Q 1/60 |
| | | | | 422/68.1 |
| 2012/0230874 | A1* | 9/2012 | Kuriger | A61B 5/1455 |
| | | | | 422/82.05 |
| 2016/0025670 | A1* | 1/2016 | O'Reilly | G01N 27/3272 |
| | | | | 29/428 |
| 2017/0120259 | A1* | 5/2017 | Takeuchi | B04B 5/02 |
| 2019/0011334 | A1* | 1/2019 | Takeuchi | A61B 5/150343 |

FOREIGN PATENT DOCUMENTS

| | | |
|---|---|---|
| JP | 2001-502793 A | 2/2001 |
| WO | 98/013684 A1 | 4/1998 |
| WO | 2016/009720 A1 | 1/2016 |

OTHER PUBLICATIONS

Written Opinion for PCT/JP2017/000177 dated Apr. 4, 2017 [PCT/ISA/237].

* cited by examiner

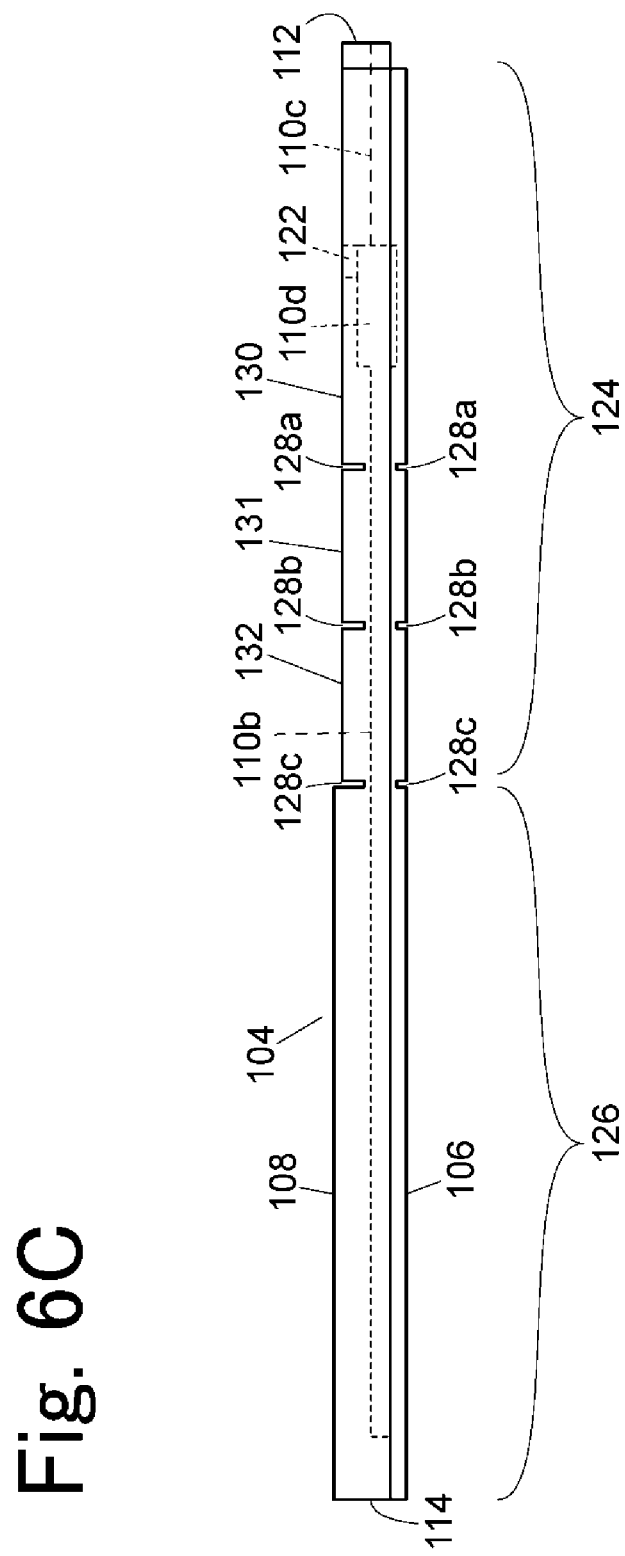

SAMPLING CHIP DIVIDING INSTRUMENT

TECHNICAL FIELD

The present invention relates to a sampling chip handling instrument that has an inlet at one end, has a flow path therein for holding samples such as blood sucked from the inlet, and is configured to be capable of dividing a certain amount of necessary portion of the sample collected in the flow path, and more particularly relates to an instrument used when dividing such sampling chips.

BACKGROUND ART

The smaller the sample volume, the more difficult it becomes to collect a small amount of blood in a conventional centrifuge tube that contains several mL or more and, after centrifugal separation treatment, separately collect a certain amount of only the plasma component of the supernatant with a micropipette or the like so that the blood cell components do not mix.

As an instrument for collecting plasma components from a small amount of blood sample, a micro blood collection tube composed of capillaries whose ends are released is used. In sampling of plasma components using a micro blood collection tube, blood is drawn into the micro blood collection tube, and the tip end is sealed by putty or the like before centrifugation. The blood collection tube is then cut by folding near the interface between the plasma part and the blood cell part, and only the plasma components are extracted by transferring them to a separately prepared capillary of fixed volume. The extracted plasma components are treated appropriately and analyzed by TLC (thin layer chromatograph), LC (liquid chromatograph), LC/MS (liquid chromatograph mass spectrometer), mass spectrometer, or the like.

A centrifuge tube has also been proposed for the purpose of collecting only a trace amount of white blood cells between the centrifuged blood cell part and the plasma part (See Patent Document 1). The centrifuge tube has a small-diameter, small-capacity reservoir between two upper and lower large-diameter reservoirs. The lower large-capacity reservoir is bottomed, and the upper large-capacity reservoir is released by an opening. After a predetermined amount of blood is collected from the upper released portion and centrifuged, the white blood cell part is supposed to come to the small-capacity reservoir. After centrifugation, a fine glass tube (capillary) is inserted from the upper released portion to collect the white blood cell component in the small-capacity reservoir.

There have also been numerous studies in which several channels including capillaries are provided in a disk, and the disk is centrifuged to separate blood components, which are then reacted with reagents for detection. As an instrument for use therein, for example, an instrument that includes an integrally-molded chamber, a channel, a reservoir, and a disk-shaped member having an analytical cell has been proposed (See Patent Document 2). A blood sample is introduced into the instrument and centrifuged to separate blood cells from serum, and the serum is then subjected to several processing steps and tests.

PRIOR ART DOCUMENTS

Patent Documents

Patent Document 1: Japanese Patent Laid-open Publication No. 01-199159

Patent Document 2: Japanese Unexamined Patent Application Publication No. 2001-502793

Patent Document 3: International Publication No. 2016/009720

SUMMARY OF THE INVENTION

Problems to be Solved by the Invention

The present inventors have proposed and carried out a sampling chip capable of accurately sampling a very small amount of sample (See Patent Document 3). The proposed sampling chip is capable of, after sampling a sample in a channel provided inside, holding the sample in a predetermined holder as it is, and performing centrifugation. The sampling chip is provided with a slit on the outer surface so that a necessary portion of the channel can be cut off by folding it with an analyst's hand, and can be divided into a plurality of parts. This makes it possible to easily extract a necessary fixed amount of the sample separated in the internal channel.

Here, when the sampling chip is divided, there is a possibility that the sample in the channel is scattered to the outside by the impact when the slit portion is broken. In particular, when handling a biological sample, it is necessary to pay attention to a scattered material because of the possibility of biohazard. In a case of dividing into a plurality of parts, there is a problem of difficulty in cutting off a part if the length of the part to be extracted is short.

Accordingly, an object of the present invention is to provide an instrument that can easily divide a sampling chip while preventing scattering of a sample inside.

Solutions to the Problems

A sampling chip dividing instrument according to the present invention is for cutting off a cut portion from a sampling chip. The sampling chip comprises a channel for collecting a sample therein and one or more of the cut portions that is cuttable at a position of a cutting slit provided on an outer surface for cutting off a part of the channel. The sampling chip is configured to allow to cut off the cut portions from the sampling chip by bending the sampling chip in a predetermined bending direction at a position of the cutting slit. The sampling chip dividing instrument comprises a main body block, a space that is provided inside the main body block, has an opening leading to an outer surface of the main body block, and fits in and contains the cut portion of the sampling chip through the opening, and a surrounding portion, which is provided outside of the space so as to surround the opening, for receiving a sample scattered from a break portion of the sampling chip divided near the opening.

It is preferable that a depth dimension of the space is designed in such away that the cutting slit, which is provided on an outer surface of the sampling chip for cutting off the cut portion from the sampling chip, is located at a position of the opening of the space or a position slightly outside the space from that position as a result of the cut portion is inserted to the end of the space. Thus, by inserting the cut portion to the end of the space, the cutting slit for cutting the cut portion is always located near the opening of the space. As a result, when the sampling chip is bent, the corner of the edge of the opening comes into contact with the vicinity of the cutting slit, and the stress concentrates on the position where the cutting slit is provided, so that the sampling chip is liable to break at the position where the cutting slit is provided. Therefore, it is possible to reliably cut off the target cut portion.

The thickness dimension of the space needs to be substantially the same as or larger than the thickness dimension of the cut portion to be fitted in the space. On the other hand, if the thickness dimension of the space is too larger than the thickness dimension of the cut portion of the sampling chip, it becomes difficult to apply stress to the target position when the sampling chip is bent. Therefore, it is preferable that the thickness dimension of the space is at most slightly larger than the thickness dimension of the cut portion to be fitted into the space. The term "slightly large" means that the gap generated between the inner wall of the space and the cut portion fitted in the space is, for example, 2 mm or less.

In a preferred embodiment of the present invention, the surrounding portion is a recess portion provided on an outer surface of the main body block and leading to the space. The recess portion has a dimension in which the sampling chip in a state where the cut portion is fitted into the space can be bent in the bending direction. According to this embodiment, since the surrounding portion can be provided by a simple construction, the sampling chip dividing instrument of the present invention can be easily and inexpensively produced.

The sampling chip dividing instrument of the present invention can also be applied to a case where the sampling chip has a plurality of the cut portions. When the sampling chip has the plurality of cut portions, the main body block is provided with a plurality of the spaces and the surrounding portions individually corresponding to the cut portions of the sampling chip.

In the above case, it is preferable that the openings of the spaces lead to different outer surfaces of the main body block from each other respectively. "The openings of the spaces lead to the main body block on side surfaces different from one another" means that the opening for inserting each cut portion of the sampling chip is provided on the plurality of surfaces of the main body block. By providing the opening for inserting the cut portion of the sampling chip to the main body block on side surfaces different from one another, the operator becomes less likely to take a wrong position (opening) at which the cut portion is inserted when cutting the cut portion.

Effects of the Invention

According to the sampling chip dividing instrument of the present invention, the sampling chip dividing instrument includes the main body block and the space that is provided inside the main body block, has the opening leading to the outer surface of the main body block, and fits in and contains the cut portion of the sampling chip through the opening. Therefore, the cut portion can be cut off from the sampling chip simply by applying a force to the sampling chip and the main body block so as to fit the cut portion of the sampling chip into the space of the main body block and bending the sampling chip. This makes it easy to cut off the cut portion from the sampling chip. In addition, the sampling chip dividing instrument of the present invention is provided with the surrounding portion that is provided outside the space so as to surround the opening for receiving a sample scattered from the break portion of the sampling chip divided near the opening. As a result, scattering of the sample to the periphery when the cut portion is cut off from the sampling chip can be prevented by the surrounding portion, thereby preventing problems such as biohazards from occurring.

BRIEF DESCRIPTION OF THE DRAWINGS

FIG. 6C is a side view of the same sampling chip.

EMBODIMENT OF THE INVENTION

Hereinafter, one embodiment of the sampling chip dividing instrument will be described with reference to the drawings.

Figure 6A:
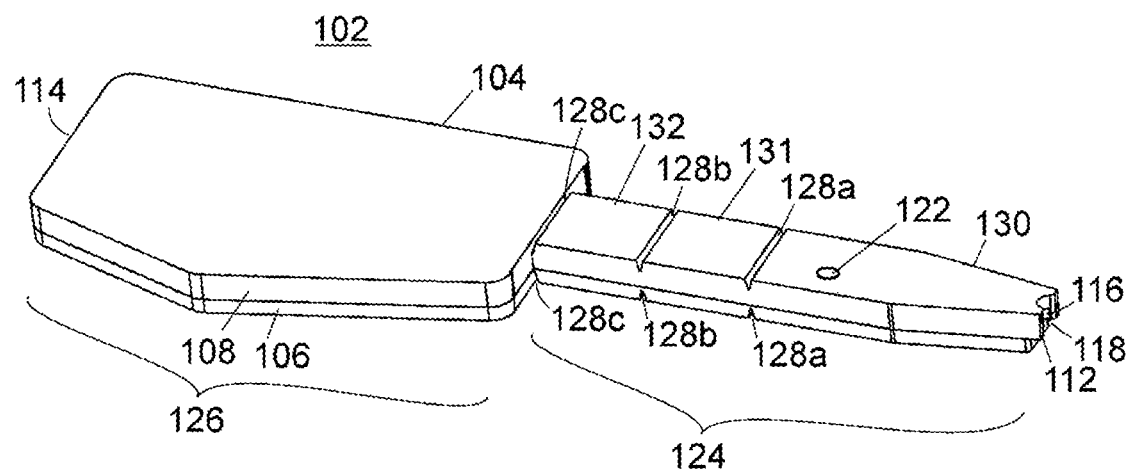
FIG. 6A is a perspective view showing an example of a sampling chip mounted on a holder of the same embodiment.
Figure 6B:
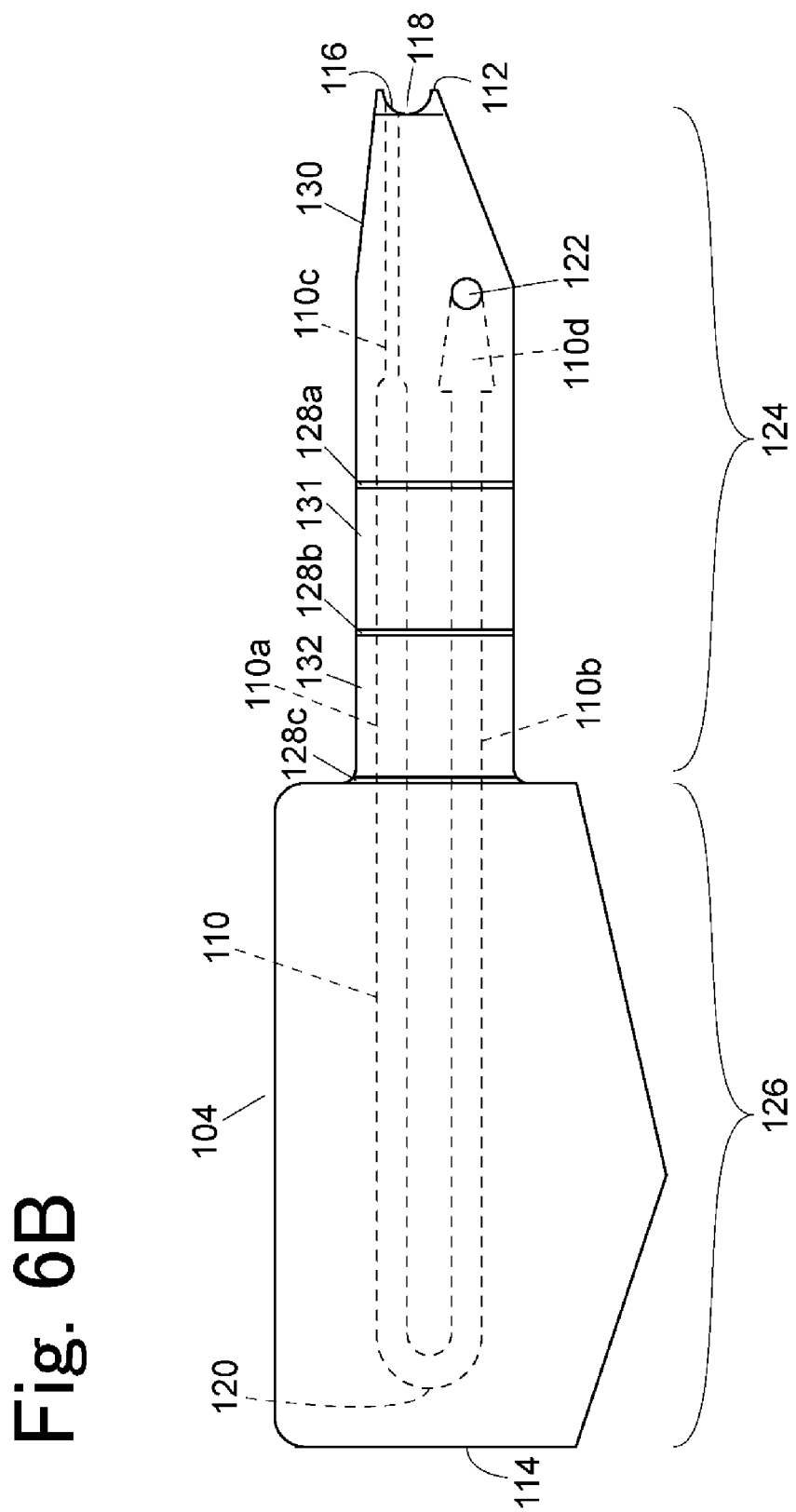
FIG. 6B is a plan view of the same sampling chip.

First, an example of the sampling chip to be subjected to the sampling chip dividing instrument will be described with reference to FIGS. 6A to 6C.

A sampling chip 102 includes a chip main body 104, and the chip main body 104 includes a lower substrate 106 and an upper substrate 108. The lower substrate 106 and the upper substrate 108 are integrated by joining to constitute the chip main body 104. A channel 110 for sampling is formed on the joining surface of the upper substrate 108, and the channel 110 is arranged in the chip main body 104 by joining the lower substrate 106 and the upper substrate 108.

The chip main body 104 has a base end 112 and a tip end 114. The sampling chip 102 is subjected to centrifugation after the sample is sucked, and the sampling chip 102 is attached to a centrifuge so that the centrifugal force acts in the direction from the base end 112 to the tip end 114. The terms "base end" and "tip end" of the chip main body 104 are determined based on the direction of the centrifugal force.

The chip main body 104 has a sample suction port 116 on the base end side. The sample suction port 116 is provided as an opening that leads to the inside of a recess portion 118 provided in the base end 112 of the chip main body 104. The recess portion 118 is for facilitating the suction of the sample through the sample suction port 116 when the tip end 114 is brought into contact with the sample such as blood at the time of sampling.

The channel 110 is thin enough to suck a sample by capillary action. The channel 110 has two channel portions 110a and 110b that are connected at a connection portion 120 on the tip end side in the chip main body 104 and extend from the tip end side to the base end side. One channel portion 110a has an introduction channel 110c, and the introduction channel 110c leads to the sample suction port 16. The other channel portion 110b terminates at a position not reaching the base end 112.

A liquid reservoir space 110d is provided at a terminal end of the channel portion 110b. The liquid reservoir space 110d has a cross-sectional area at least at its inlet portion (tip portion on the tip end side of the liquid reservoir space 10d) with a size so as not to suck liquid by capillary action, and an air hole 122 leads to the base end portion of the liquid reservoir space 110d. The liquid reservoir space 110d has an internal capacity equal to or larger than an internal capacity of a portion of the introduction channel 110c of the channel portion 110a located more on the base end side (upper side in the figure) than the air hole 122.

The cross-sectional area of the inlet portion of the liquid reservoir space 110d is, for example, twice or more the cross-sectional area of the other portion of the channel portion 110b. An example of the cross-sectional dimensions of the inlet portion of the liquid reservoir space 10d is about 3 mm in width and 1.5 mm in depth.

Advantages of providing the liquid reservoir space 110d at the terminal end of the channel portion 110b include the following.

First, since the liquid reservoir space 110d does not suck the sample by the capillary action, the sample sucked from the sample suction port 116 stops at the inlet portion of the liquid reservoir space 110d without reaching the position of the air hole 122. Thus, the amount of sampling into the channel portions 110a and 110b can be secured without increasing the amount of sampling into an extraction portion 110.

Since the sample sucked from the sample suction port 116 stops at the inlet portion of the liquid reservoir space 110d, there is no sample in the liquid reservoir space 110d before the centrifugation is performed. By making the inner surface of the liquid reservoir space 110d hydrophobic, the sample can be stopped more reliably at the inlet portion of the liquid reservoir space 110d. When centrifugation is performed in this state, the sample that becomes a surplus because of the sample becoming an equilibrium state is stored in the liquid reservoir space 110d. Since the internal capacity of the liquid reservoir space 110d is equal to or larger than the internal capacity of the portion of the introduction channel 110c of the channel portion 110a located more on the base end side (upper side in the figure) than the air hole 122, all the surplus samples are stored in the liquid reservoir space 110d. As a result, it is possible to suppress the surplus sample from overflowing from the channel portion 110b and being discharged from the air hole 122.

The sampling chip 102 of this embodiment is provided with a sampling portion 124 on the base side and a wide portion 126 on the tip side. The width and thickness dimensions of the sampling portion 124 are smaller than the width and thickness dimensions of the wide portion 126. Each of the upper and the lower surfaces of the sampling portion 124 are provided with three cutting slits 128a, 128b, and 128c that are perpendicular to the direction in which the sampling portion 124 (the channel 110) extends. The cutting slit 128c is provided at a boundary portion between the sampling portion 124 and the wide portion 126. The cutting slit 128a is provided at a position more on the tip side than the air hole 122, and the cutting slit 128b is provided at a position between the cutting slits 128a and 128c.

By providing the cutting slits 128a, 128b, and 128c at the three positions of the sampling section 124, the sampling section 124 can be divided into three cut portions 130, 131, and 132. The cut portion 130 can be cut if stress is applied to the sampling chip 102 so as to be folded at the position of the cutting slit 126a, the cut portion 131 can be cut if stress is applied so as to be folded at the position of the cutting slit 126b, and the cut portion 132 can be cut if stress is applied so as to be folded at the position of the cutting slit 126c.

The cut portions 131 and 132 include the channel portions 110a and 110b, and by cutting off the cut portions 131 and 132, a certain amount of sample held in the channel portions 110a and 110b of the cut portions 131 and 132 can be easily extracted.

Since the positions at which the cut portions 131 and 132 are arranged in the sampling portion 124 are on the base end side, when the sample is centrifuged, the centrifuged component having the smaller specific gravity is located in the cut portions 131 and 132. For example, when blood is sampled and centrifuged so that the direction from the base end to the tip end of the sampling chip 102 is in the direction of application of the centrifugal force, the positions of the cut portions 131 and 132 in the channel 110 are set so that plasma components or serum components locate at the cut portions 131 and 132.

The wide portion 126 has such a size that identification information such as the name and the number of a sample collected on the sampling chip can be written or a label on which the identification information is written can be attached. The wide portion 126 can also be used as a grip portion for holding the sampling chip.

The sampling chip 102 is made of, for example, a resin material. The resin material is not particularly limited, but, for example, COP (cycloolefin polymer), PMMA (polymethyl methacrylate resin), PP (Polypropylene resin), PC (polycarbonate resin), PVA (polyvinyl alcohol), and the like can be used.

Since the channel 110 is for sucking the liquid sample from the sample suction port 116 by capillary action, it is necessary not only that the cross-sectional area of the channel 110 is narrow enough to cause capillary action but also that if the sample is blood or aqueous solution, the inner surface of the channel 110 must be hydrophilic. Since the resin materials exemplified above are hydrophobic, the inner surface of the channel 110 and the sample suction port 116 are preferably treated so as to be hydrophilic.

In a case where the sample is blood, it is preferable that an anticoagulant that prevents blood coagulation is provided on the inner surface of the channel 110 in order to suck the blood directly from the specimen and collect the plasma to the cut portion 130 by centrifugation. The anticoagulant may be coated on the inner surface of the channel 110 after a hydrophilic polymer is coated thereon.

In the sampling chip 102, in order to use the cut portions 131 and 132 for analysis after centrifugation, the cut portions 131 and 132 are cut off from the chip main body 104 to form individual cut portions 131 and 132. In order to cut off the cut portions 130, 131, and 132 from the sampling chip 102, the chip main body 104 is folded in order at the positions of the cutting slits 128a, 128b, and 128c. In this way, two analytical samples can be obtained from one chip main body 104. In general, the cut portion 130 on the most base side becomes an unnecessary portion, and this it is discarded.

Figure 1A:
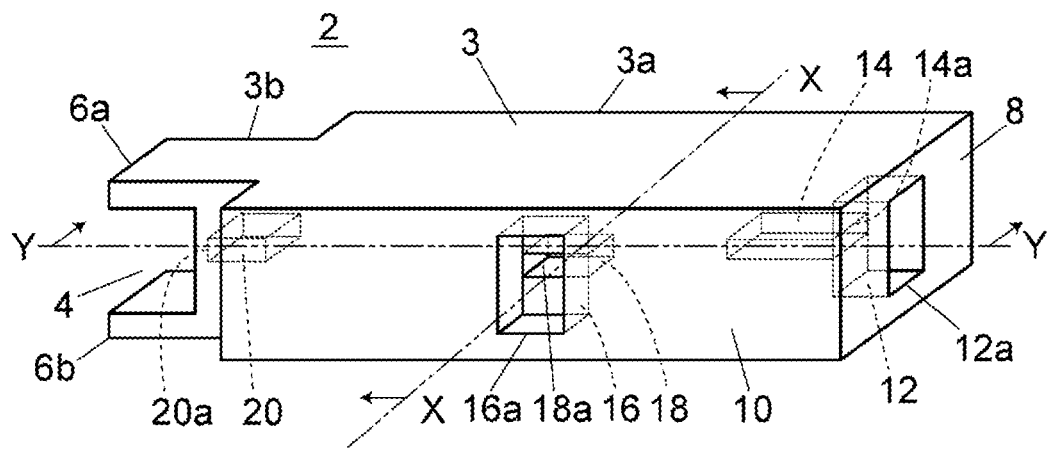
FIG. 1A is a perspective view showing one embodiment of a sampling chip dividing instrument.
Figure 1B:
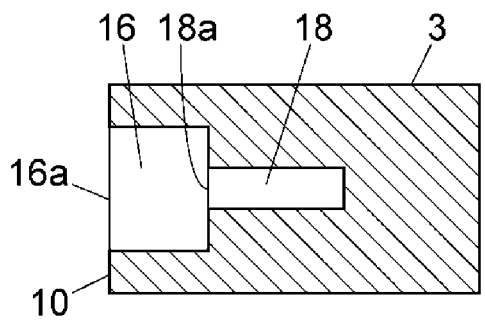
FIG. 1B is a sectional view at the X-X position of FIG. 1A.
Figure 1C:
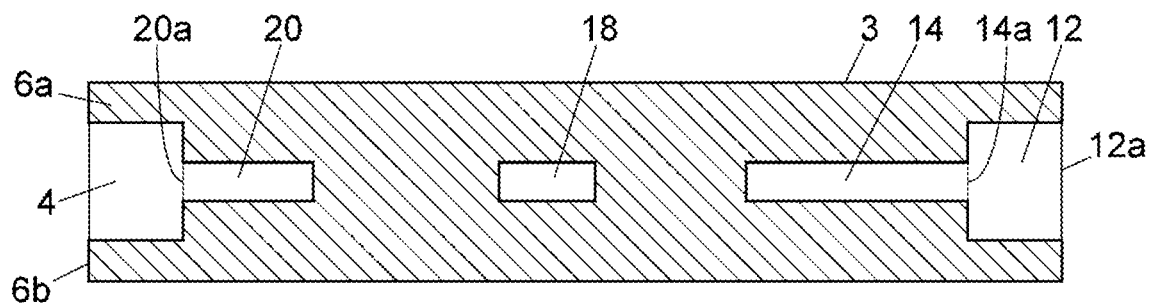
FIG. 1C is a sectional view at the Y-Y position of FIG. 1A.

Next, one embodiment of a sampling chip dividing instrument for assisting in cutting off each of the cut portions 130, 131, and 132 from the sampling chip 102 will be described with reference to FIGS. 1A to 1C.

A sampling chip dividing instrument 2 according to this embodiment includes a main body block 3, spaces 14, 18, and 20 that are provided inside the main body block 3, and recess portions 4, 12, and 16 that are provided on the outer surface of the main body block 3 to form a surrounding portion. The material of the main body block 3 may be anything such as vinyl chloride or polypropylene, as long as it is as hard as or harder than the sampling chip 102.

The main body block 3 includes a substantially rectangular parallelepiped portion 3a and a narrow portion 3b that has a width dimension smaller than the substantially rectangular parallelepiped portion 3a and projects from one end of the substantially rectangular parallelepiped portion 3a. In the following description, the side where the narrow portion 3b is provided in the main body block 3 is referred to as the tip end side, and the side opposite to the narrow portion 3b is referred to as the base end side. The recess portion 4 is provided in a tip end surface of the narrow portion 3b of the main body block 3 over the entire width of the narrow portion 3b. Thus, the narrow portion 3b has a U-shaped cross section. The bottom surface of the recess portion 4 of the narrow portion 3b is provided with an opening 20a that leads to the space 20.

A side surface 8 on the base end side of the main body block 3 is provided with a rectangular opening 12a that leads to the recess portion 12. The deepest surface of the recess portion 12 is provided with an opening 14a that leads to the space 14. A side surface 10 orthogonal to the surface 8 of the main body block 3 is provided with a rectangular opening 16a that leads to the recess portion 16. The deepest surface of the recess portion 16 is provided with an opening 18a that leads to the space 18.

Figure 2A:
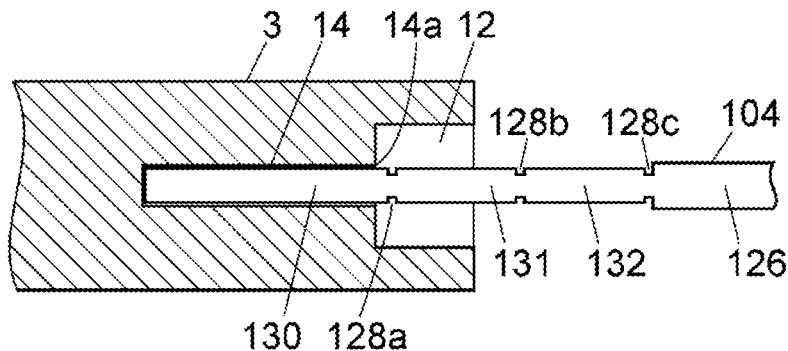
FIG. 2A is a sectional view showing a state in which a first cut portion of a sampling chip is fitted in a first space of the same embodiment.
Figure 2B:
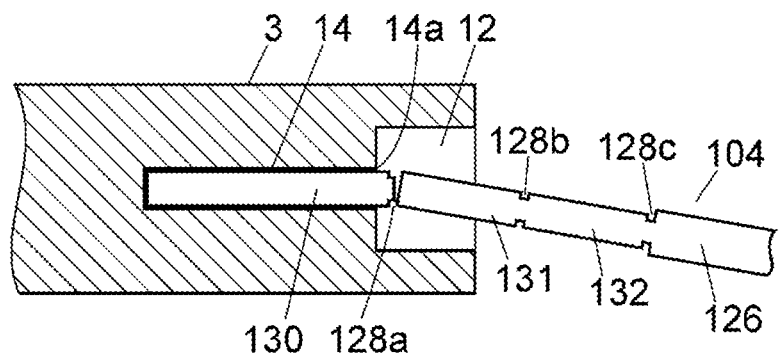
FIG. 2B is a sectional view showing a state in which the first cut portion of the sampling chip is fitted in the first space of the same embodiment and the sampling chip is about to be bent.

As shown in FIG. 2A, the space 14 is for fitting the cut portion 130 (See FIGS. 6A to 6C) located nearest to the base end of the sampling chip 102. As shown in FIG. 2B, the space 14 is used to cut off the cut portion 130 from the sampling chip 102 by inserting the cut portion 130 and folding the chip main body 104 of the sampling chip 102 at the position of the cutting slit 28a. The height dimension (dimension in the vertical direction in FIGS. 1C and 2B) of the recess portion 12 is designed to be a dimension such that the chip main body 104 in a state where the cut portion 130 is fitted in the space 14 can be folded at the position of the cutting slit 28a.

The depth dimension (dimension in the horizontal direction in FIG. 1C) of the space 14 is designed to be slightly shorter (for example, about 1 mm) than the length dimension of the cut portion 130. As a result, when the cut portion 130 is fitted into the depth of the space 14, the cutting slit 28a is disposed at a position inside the recess portion 12 slightly outside the edge of the opening 14a of the space 14. Thus, as shown in FIG. 2B, when the main body chip 104 is bent at the position of the cutting slit 28a, the inner circumferential surface of the recess portion 12 receives the liquid scattered from the broken surface, and the liquid is prevented from being scattered to the surroundings.

The height dimension (dimension in the vertical direction in FIG. 1C) of the space 14 may be designed to be substantially the same as, slightly larger than, or slightly smaller (for example, 0.1 mm) than, the thickness dimension of the cut portion 130. Since the cut portion 130 is an unnecessary portion that is not used for analysis, it may remain stored inside the main body block 3. Therefore, if the height dimension of the space 14 is designed to be slightly smaller than the thickness dimension of the cut portion 130, the chip main body 130 after being cut off from the cut portion 104 can be left in the main body block 3.

Figure 3A:
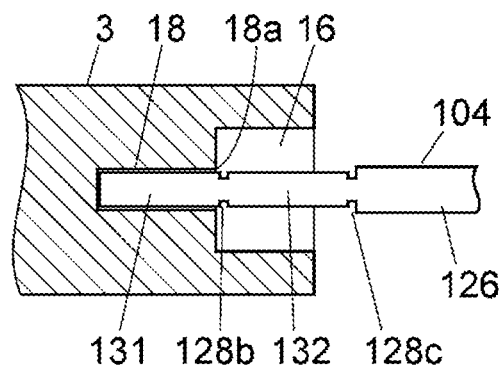
FIG. 3A is a sectional view showing a state in which a second cut portion of the sampling chip is fitted in a second space of the same embodiment.
Figure 3B:
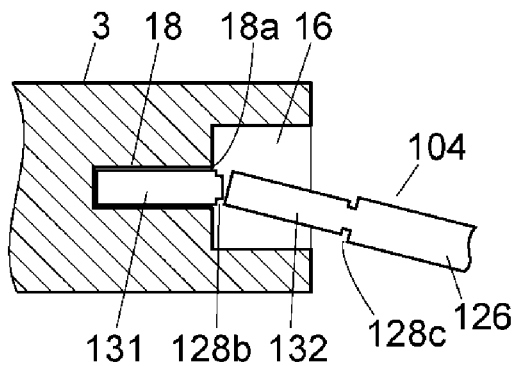
FIG. 3B is a sectional view showing a state in which the second cut portion of the sampling chip is fitted in the second space of the same embodiment and the sampling chip is about to be bent.

As shown in FIG. 3A, the space 18 is for fitting the cut portion 131 (See FIGS. 6A to 6C) of the sampling chip 102 after the cut portion 130 is cut off. As shown in FIG. 3B, the space 18 is used to cut off the cut portion 131 from the sampling chip 102 by inserting the cut portion 131 and bending the chip main body 104 at the position of the cutting slit 28b. The height dimension (dimension in the vertical direction in FIGS. 1B and 3B) of the recess portion 16 is designed to be a dimension in such a way that the chip main body 104 in a state where the cut portion 131 is fitted in the space 16 can be bent at the position of the cutting slit 28b.

The depth dimension (dimension in the horizontal direction in FIG. 1B) of the space 18 is designed to be slightly shorter (for example, about 1 mm) than the length dimension of the cut portion 131. As a result, when the cut portion 131 is fitted into the end of the space 18, the cutting slit 28b is disposed at a position inside the recess portion 16 slightly outside the edge of the opening 18a of the space 18. Thus, as shown in FIG. 3B, when the main body chip 104 is bent at the position of the cutting slit 28b, the inner circumferential surface of the recess portion 16 receives the liquid scattered from the broken surface, and the liquid is prevented from being scattered to the surroundings.

The height dimension (dimension in the vertical direction in FIG. 1B) of the space 18 is designed to be substantially the same as or slightly larger than the thickness dimension of the cut portion 131 so that the cut portion 131 having been cut can be extracted of the space 18.

Figure 4A:
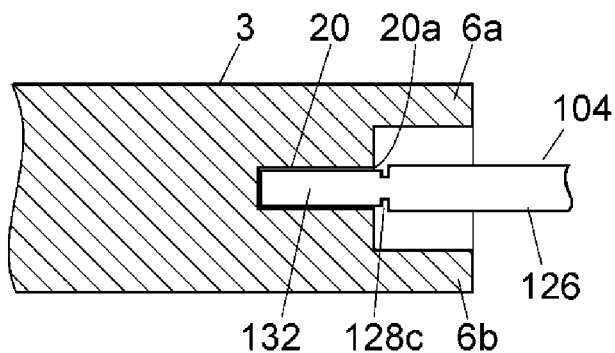
FIG. 4A is a sectional view showing a state in which a third cut portion of the sampling chip is fitted in a third space of the same embodiment.
Figure 4B:
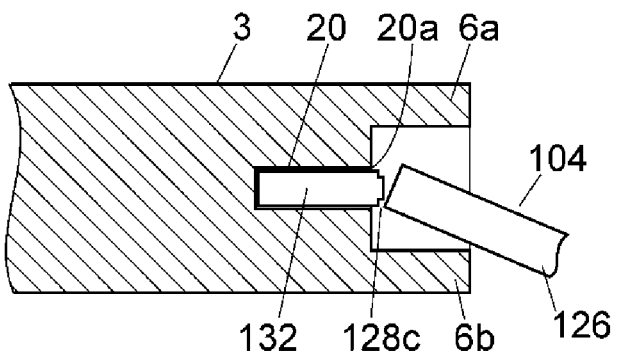
FIG. 4B is a sectional view showing a state in which the third cut portion of the sampling chip is fitted in the third space of the same embodiment and the sampling chip is about to be bent.

As shown in FIG. 4A, the space 20 is for fitting the cut portion 132 (See FIGS. 6A to 6C) of the sampling chip 102 after the cut portion 131 is cut off. As shown in FIG. 4B, the space 20 is used to cut off the cut portion 132 from the sampling chip 102 by inserting the cut portion 132 and folding the chip main body 104 at the position of the cutting slit 28c. The height dimension (dimension in the vertical direction in FIGS. 1C and 4B) of the recess portion 4 is designed to be a dimension such that the chip main body 104 in a state where the cut portion 132 is fitted in the space 20 can be folded at the position of the cutting slit 28c.

The depth dimension (dimension in the horizontal direction in FIG. 1C) of the space 20 is designed to be slightly shorter (for example, about 1 mm) than the length dimension of the cut portion 132. As a result, when the cut portion 132 is fitted into the end of the space 20, the cutting slit 28c is disposed at a position inside the recess portion 4 slightly outside the edge of the opening 20a of the space 20. Thus, as shown in FIG. 4B, when the main body chip 104 is folded at the position of the cutting slit 28c, protrusions 6a and 6b sandwiching the recess portion 4 act as eaves and receive the liquid scattered from the broken surface, and the liquid is prevented from being scattered to the surroundings.

The height dimension (dimension in the vertical direction in FIG. 1B) of the space 20 is designed to be substantially the same as or slightly larger than the thickness dimension of the cut portion 132 so that the cut portion 132 having been cut can be extracted of the space 20.

In the sampling chip dividing instrument 2 according to the above embodiment, the recess portions 12, 16, and 4 are provided on the outer surface of the main body block 3, and spaces 14, 18, and 20 are provided on the deeper side than those recess portions, so that the inner surfaces of the recess portions 12, 16, and 4 are used as a surrounding portion for receiving the liquid scattered from the broken surface of the main body chip 104.

However, in the present invention, the surrounding portion for receiving the liquid scattered from the broken surface of the main body chip 104 is not limited to such recess portion.

Figure 5:
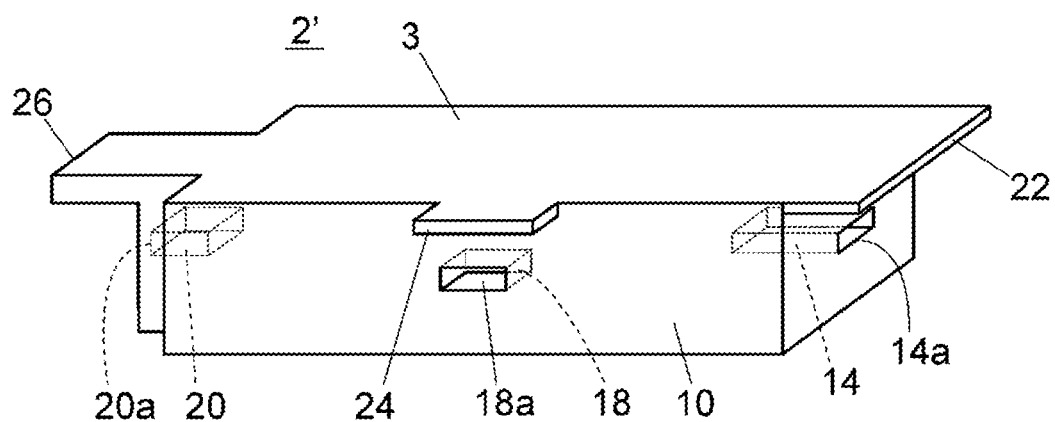
FIG. 5 is a perspective view showing another embodiment of the sampling chip dividing instrument.

For example, in a sampling chip dividing instrument 2' of the embodiment shown in FIG. 5, openings 14a, 18a, and 20a that lead to the spaces 14, 18, and 20 are provided on the outer surface of the main body block 3. At the positions corresponding to the respective openings 14a, 18a, and 20a, the side surfaces of the main body block 3 where the openings 14a, 18a, and 20a are provided are provided with eaves 22, 24, and 26 that protrude from the respective side surfaces for receiving the liquid scattered from the broken surface of the main body chip 104. The eaves 22, 24, and 26 are provided only on one side of the openings 14a, 18a, and 20a in the embodiment shown in FIG. 5, but they may be provided so as to sandwich the openings 14a, 18a, and 20a.

The spaces 14, 18, and 20 are provided so as to lead to side surfaces different from one another of the main body block 3 in the sampling chip dividing instruments 2 and 2' of the embodiment described above, but the present invention is not limited thereto, and they may be provided so as to lead to side surface identical to one another.

DESCRIPTION OF REFERENCE SIGNS 2, 2': Sampling chip dividing instrument
3: Main body block
3a: Rectangular parallelepiped portion
3b: Narrow portion
4, 12, 16: Recess portions
6a, 6b: Protrusions
8, 10: Side surfaces of the main body block
14, 16, 20: Spaces
22, 24, 26: Eaves
102: Sampling chip
104: Chip main body
110: Channel
110a, 110b: Channel portions
110c: Introduction channel
112: Base end
114: Tip end
116: Sample suction port
122: Air hole
128a, 128b, 128c: Cutting slits
130, 131, 132: Cut sections

The invention claimed is:

1. A sampling chip dividing system comprising:
a sampling chip dividing instrument configured to cut off one or more cut portions from a sampling chip; and
a sampling chip comprising a channel configured to collect a sample therein and one or more of the cut portions configured to be cuttable at a position of a corresponding one or more cutting slits provided on an outer surface for cutting off a part of the channel, and the cutting slits are configured to cut off a corresponding one of the one or more of the cut portions from the sampling chip by bending the sampling chip in a predetermined bending direction at a position of the cutting slit, and wherein
the sampling chip dividing instrument is comprising:
a main body block;
a space that is provided inside the main body block, has an opening leading to an outer surface of the main body block, and fits in and contains one of the cut portions of the sampling chip through the opening; and
a surrounding portion, which is provided outside of the space so as to surround the opening, and configured to receive a sample scattered from a cut off portion of the sampling chip divided near the opening,
wherein a depth dimension of the space is designed in such a way that the cutting slit, which is provided on the outer surface of the sampling chip for cutting off the one or more of the cut portions from the sampling chip, is located at a position of the opening of the space or a position slightly outside the space from that position as a result of the one of the cut portions being inserted to the end of the space.

2. The sampling chip dividing system according to claim 1, wherein
a thickness dimension of the space is substantially the same as or slightly larger than a thickness dimension of the one of the cut portions.

3. The sampling chip dividing system according to claim 1, wherein
the sampling chip has a plurality of cut portions; and
the main body block is provided with a plurality of the spaces and the surrounding portions individually corresponding to the cut portions of the sampling chip.

4. The sampling chip dividing system according to claim 3, wherein the openings of the spaces lead to different outer surfaces of the main body block from each other respectively.

5. The sampling chip dividing system according to claim 1, wherein the sampling chip contains a sample.

6. A sampling chip dividing system comprising:
a sampling chip dividing instrument configured to cut off one or more cut portions from a sampling chip; and
a sampling chip comprising a channel configured to collect a sample therein and one or more of the cut portions configured to be cuttable at a position of a corresponding one or more cutting slits provided on an outer surface for cutting off a part of the channel, and the cutting slits are configured to cut off a corresponding one of the one or more of the cut portions from the sampling chip by bending the sampling chip in a predetermined bending direction at a position of the cutting slit, and wherein
the sampling chip dividing instrument comprises:
a main body block;
a space that is provided inside the main body block, has an opening leading to an outer surface of the main body block, and fits in and contains one of the cut portions of the sampling chip through the opening; and
a surrounding portion, which is provided outside of the space so as to surround the opening, and configured to receive a sample scattered from a cut off portion of the sampling chip divided near the opening, wherein
the surrounding portion is a recess portion provided on an outer surface of the main body block and leading to the space, and the recess portion has a dimension in which the sampling chip in a state where the one of the cut portions is fitted into the space can be bent in the bending direction.

* * * * *